(12) United States Patent
Domankevitz et al.

(10) Patent No.: US 7,891,362 B2
(45) Date of Patent: Feb. 22, 2011

(54) METHODS FOR TREATING PIGMENTARY AND VASCULAR ABNORMALITIES IN A DERMAL REGION

(75) Inventors: Yacov Domankevitz, Newton, MA (US); Edward Victor Ross, Jr., San Diego, CA (US)

(73) Assignee: Candela Corporation, Wayland, MA (US)

( * ) Notice: Subject to any disclaimer, the term of this patent is extended or adjusted under 35 U.S.C. 154(b) by 822 days.

(21) Appl. No.: 11/645,222

(22) Filed: Dec. 22, 2006

(65) Prior Publication Data

US 2007/0198003 A1 Aug. 23, 2007

Related U.S. Application Data

(60) Provisional application No. 60/753,821, filed on Dec. 23, 2005.

(51) Int. Cl.
*A61B 19/00* (2006.01)
(52) U.S. Cl. .............. 128/898; 606/3; 606/9; 607/88
(58) Field of Classification Search .......... 128/898
See application file for complete search history.

(56) References Cited

U.S. PATENT DOCUMENTS

| 3,404,350 | A | 10/1968 | Muncheryan |
| 3,538,919 | A | 11/1970 | Meyer et al. |
| 3,693,623 | A | 9/1972 | Harte et al. |
| 3,769,963 | A | 11/1973 | Goldman et al. |
| 3,834,391 | A | 9/1974 | Block |
| 3,900,034 | A | 8/1975 | Katz et al. |
| 3,916,143 | A | 10/1975 | Farrell |
| 4,388,924 | A | 6/1983 | Weissman et al. |
| 4,461,294 | A | 7/1984 | Baron |
| 4,608,978 | A | 9/1986 | Rohr |

(Continued)

FOREIGN PATENT DOCUMENTS

CA 1041610 10/1978

(Continued)

OTHER PUBLICATIONS

Marina Plastic Surgery Associates Medical Corporation, Facial Veins—Los Angeles Facial Vein Treatment—Reduce Redness, Rosacea, Telangiectasia [online], [retrived on Jun. 8, 2009]. Retrived from the Internet <URL:http://www.marinaplasticsurgery.com/plastic_surgery/facial_veins.cfm>.*

(Continued)

*Primary Examiner*—Ahmed M Farah
(74) *Attorney, Agent, or Firm*—Proskauer Rose LLP (57) ABSTRACT

A beam of radiation can be provided to treat a dermatological condition in a target region of skin. The beam of radiation can have a wavelength between about 700 nm and about 800 nm, a fluence greater than about 50 J/cm$^2$, and a pulse duration between about 10 msec and about 300 msec. The beam of radiation is delivered to the target region of skin to affect (i) at least one pigmentary abnormality disposed in an epidermal region of the target region and (ii) at least one vascular abnormality disposed in a dermal region of the target region. A surface of the epidermal region of the target region of skin can be cooled to prevent substantial unwanted injury to at least a portion of the epidermal region.

27 Claims, 2 Drawing Sheets

U.S. PATENT DOCUMENTS

| | | | |
|---|---|---|---|
| 4,617,926 A | 10/1986 | Sutton | |
| 4,733,660 A | 3/1988 | Itzkan | |
| 4,819,669 A | 4/1989 | Politzer | |
| 4,854,320 A | 8/1989 | Dew et al. | |
| 4,905,690 A | 3/1990 | Ohshiro et al. | |
| 4,930,504 A | 6/1990 | Diamantopoulos et al. | |
| 4,976,709 A | 12/1990 | Sand | |
| 4,985,027 A | 1/1991 | Dressel | |
| 5,000,752 A | 3/1991 | Hoskin et al. | |
| 5,002,051 A | 3/1991 | Dew et al. | |
| 5,019,034 A | 5/1991 | Weaver et al. | |
| 5,050,597 A | 9/1991 | Daikuzono | |
| 5,057,104 A | 10/1991 | Chess | |
| 5,059,192 A | 10/1991 | Zaias | |
| 5,102,410 A | 4/1992 | Dressel | |
| 5,112,328 A | 5/1992 | Tabaoda et al. | |
| 5,133,708 A | 7/1992 | Smith | |
| 5,137,530 A | 8/1992 | Sand | |
| 5,139,495 A | 8/1992 | Daikuzono | |
| 5,140,984 A | 8/1992 | Dew et al. | |
| 5,143,063 A | 9/1992 | Fellner | |
| 5,151,098 A | 9/1992 | Loertscher | |
| 5,165,418 A | 11/1992 | Tankovich | |
| 5,182,857 A | 2/1993 | Simon | |
| 5,190,032 A | 3/1993 | Zacoi | |
| 5,226,907 A | 7/1993 | Tankovich | |
| 5,282,797 A | 2/1994 | Chess | |
| 5,290,273 A * | 3/1994 | Tan | 606/9 |
| 5,304,169 A | 4/1994 | Sand | |
| 5,304,170 A | 4/1994 | Green | |
| 5,312,395 A | 5/1994 | Tan et al. | |
| 5,320,618 A | 6/1994 | Gustafsson | |
| 5,334,190 A | 8/1994 | Seiler | |
| 5,336,217 A | 8/1994 | Buys et al. | |
| 5,344,418 A | 9/1994 | Ghaffari | |
| 5,348,551 A | 9/1994 | Spears et al. | |
| 5,360,425 A | 11/1994 | Cho | |
| 5,374,265 A | 12/1994 | Sand | |
| 5,394,492 A | 2/1995 | Hwang | |
| 5,397,327 A | 3/1995 | Koop et al. | |
| 5,405,368 A | 4/1995 | Eckhouse | |
| 5,409,479 A | 4/1995 | Dew et al. | |
| 5,423,803 A | 6/1995 | Tankovich et al. | |
| 5,425,728 A | 6/1995 | Tankovich | |
| 5,437,658 A | 8/1995 | Muller et al. | |
| 5,445,146 A | 8/1995 | Bellinger | |
| 5,445,634 A | 8/1995 | Keller | |
| 5,454,840 A | 10/1995 | Krakovsky et al. | |
| 5,464,436 A | 11/1995 | Smith | |
| 5,474,549 A | 12/1995 | Ortiz et al. | |
| 5,484,432 A | 1/1996 | Sand | |
| 5,486,172 A | 1/1996 | Chess | |
| 5,522,813 A | 6/1996 | Trelles | |
| 5,527,350 A | 6/1996 | Grove et al. | |
| 5,569,242 A | 10/1996 | Lax et al. | |
| 5,595,568 A | 1/1997 | Anderson et al. | |
| 5,606,798 A | 3/1997 | Kelman | |
| 5,614,339 A | 3/1997 | Tankovich | |
| 5,647,866 A | 7/1997 | Zaias et al. | |
| 5,653,706 A | 8/1997 | Zavislan et al. | |
| 5,683,380 A | 11/1997 | Eckhouse et al. | |
| 5,707,403 A | 1/1998 | Grove et al. | |
| 5,713,845 A | 2/1998 | Tankovich | |
| 5,735,844 A | 4/1998 | Anderson et al. | |
| 5,746,736 A | 5/1998 | Tankovich | |
| 5,749,868 A | 5/1998 | Furumoto | |
| 5,752,948 A | 5/1998 | Tankovich et al. | |
| 5,752,949 A | 5/1998 | Tankovich et al. | |
| 5,755,753 A | 5/1998 | Knowlton | |
| 5,807,385 A | 9/1998 | Keller | |
| 5,810,801 A | 9/1998 | Anderson et al. | |
| 5,814,040 A | 9/1998 | Nelson et al. | |
| 5,817,089 A | 10/1998 | Tankovich et al. | |
| 5,820,626 A | 10/1998 | Baumgardner | |
| 5,843,072 A | 12/1998 | Furumoto et al. | |
| 5,860,967 A | 1/1999 | Zavislan et al. | |
| 5,868,732 A | 2/1999 | Waldman et al. | |
| 5,871,480 A | 2/1999 | Tankovich | |
| 5,897,549 A | 4/1999 | Tankovich | |
| 5,925,035 A | 7/1999 | Tankovich | |
| 5,954,710 A | 9/1999 | Paolini et al. | |
| 5,964,749 A * | 10/1999 | Eckhouse et al. | 606/9 |
| 5,968,034 A * | 10/1999 | Fullmer et al. | 606/9 |
| 5,979,454 A | 11/1999 | Anvari et al. | |
| 5,997,530 A | 12/1999 | Nelson et al. | |
| 6,030,378 A | 2/2000 | Stewart | |
| 6,036,684 A | 3/2000 | Tankovich et al. | |
| 6,050,990 A | 4/2000 | Tankovich et al. | |
| 6,063,074 A | 5/2000 | Tankovich | |
| 6,077,294 A | 6/2000 | Cho et al. | |
| 6,083,217 A | 7/2000 | Tankovich | |
| 6,096,029 A | 8/2000 | O'Donnell, Jr. | |
| 6,106,514 A | 8/2000 | O'Donnell, Jr. | |
| 6,106,516 A | 8/2000 | Massengill | |
| 6,120,497 A | 9/2000 | Anderson et al. | |
| 6,120,519 A | 9/2000 | Weber et al. | |
| 6,152,917 A | 11/2000 | Tankovich | |
| 6,162,211 A * | 12/2000 | Tankovich et al. | 606/9 |
| 6,168,590 B1 | 1/2001 | Neev | |
| 6,171,301 B1 | 1/2001 | Nelson et al. | |
| 6,183,773 B1 | 2/2001 | Anderson | |
| 6,206,873 B1 | 3/2001 | Paolini et al. | |
| 6,235,016 B1 | 5/2001 | Stewart | |
| 6,248,103 B1 | 6/2001 | Tannenbaum et al. | |
| 6,267,771 B1 | 7/2001 | Tankovich et al. | |
| 6,273,883 B1 * | 8/2001 | Furumoto | 606/9 |
| 6,273,884 B1 | 8/2001 | Altshuler et al. | |
| 6,280,438 B1 | 8/2001 | Eckhouse et al. | |
| 6,302,863 B1 | 10/2001 | Tankovich | |
| 6,315,756 B1 | 11/2001 | Tankovich | |
| 6,350,276 B1 | 2/2002 | Knowlton | |
| 6,383,176 B1 * | 5/2002 | Connors et al. | 606/9 |
| 6,387,089 B1 | 5/2002 | Kreindel et al. | |
| 6,405,090 B1 | 6/2002 | Knowlton | |
| 6,408,212 B1 | 6/2002 | Neev | |
| 6,436,094 B1 | 8/2002 | Reuter | |
| 6,511,475 B1 | 1/2003 | Altshuler et al. | |
| 6,517,532 B1 | 2/2003 | Altshuler et al. | |
| 6,530,920 B1 | 3/2003 | Whitcroft et al. | |
| 6,533,776 B2 * | 3/2003 | Asah et al. | 606/9 |
| 6,562,054 B1 | 5/2003 | Weber et al. | |
| 6,569,156 B1 | 5/2003 | Tankovich et al. | |
| 6,600,951 B1 | 7/2003 | Anderson | |
| 6,605,079 B2 | 8/2003 | Shanks et al. | |
| 6,605,080 B1 | 8/2003 | Altshuler et al. | |
| 6,610,052 B2 | 8/2003 | Furumoto | |
| 6,613,040 B2 | 9/2003 | Tankovich et al. | |
| 6,613,042 B1 | 9/2003 | Tankovich et al. | |
| 6,632,219 B1 | 10/2003 | Baranov et al. | |
| 6,648,904 B2 | 11/2003 | Altshuler et al. | |
| 6,659,999 B1 | 12/2003 | Anderson et al. | |
| 6,663,658 B1 | 12/2003 | Kollias et al. | |
| 6,723,090 B2 | 4/2004 | Altshuler et al. | |
| 6,733,492 B2 | 5/2004 | Ota et al. | |
| 6,743,222 B2 * | 6/2004 | Durkin et al. | 606/9 |
| 6,746,444 B2 * | 6/2004 | Key | 606/9 |
| 6,807,297 B1 | 10/2004 | Tankovich et al. | |
| 6,920,883 B2 | 7/2005 | Bessette et al. | |
| 6,926,683 B1 | 8/2005 | Kochman et al. | |
| 6,997,923 B2 | 2/2006 | Anderson et al. | |
| 7,020,528 B2 | 3/2006 | Neev | |
| 7,033,349 B2 * | 4/2006 | Key | 606/9 |
| 7,060,061 B2 | 6/2006 | Altshuler et al. | |
| 7,090,670 B2 | 8/2006 | Sink | |

| | | | |
|---|---|---|---|
| 7,118,563 B2 | 10/2006 | Weckwerth et al. | |
| 7,184,614 B2 | 2/2007 | Slatkine | |
| 2002/0161357 A1 | 10/2002 | Anderson et al. | |
| 2002/0169442 A1 | 11/2002 | Neev | |
| 2002/0173780 A1 | 11/2002 | Altshuler et al. | |
| 2002/0183789 A1 | 12/2002 | Neev | |
| 2003/0032950 A1 | 2/2003 | Altshuler et al. | |
| 2003/0036749 A1 | 2/2003 | Durkin et al. | |
| 2003/0216719 A1 | 11/2003 | Debenedictis et al. | |
| 2004/0005349 A1 | 1/2004 | Neev | |
| 2004/0036975 A1 | 2/2004 | Slatkine | |
| 2004/0039312 A1 | 2/2004 | Hillstead et al. | |
| 2004/0073079 A1 | 4/2004 | Altshuler et al. | |
| 2004/0093042 A1 | 5/2004 | Altshuler et al. | |
| 2004/0143247 A1 | 7/2004 | Anderson et al. | |
| 2004/0167499 A1 | 8/2004 | Grove et al. | |
| 2004/0167501 A1 | 8/2004 | Island et al. | |
| 2004/0167592 A1 | 8/2004 | Grove et al. | |
| 2004/0176754 A1 | 9/2004 | Island et al. | |
| 2004/0176823 A1 | 9/2004 | Island et al. | |
| 2004/0176824 A1 | 9/2004 | Weckwerth et al. | |
| 2004/0217675 A1 | 11/2004 | Desilets et al. | |
| 2005/0049582 A1* | 3/2005 | DeBenedictis et al. | 606/9 |
| 2005/0055055 A1 | 3/2005 | Neev | |
| 2005/0102009 A1 | 5/2005 | Costantino | |
| 2005/0131439 A1 | 6/2005 | Brett | |
| 2005/0215987 A1 | 9/2005 | Slatkine | |
| 2005/0234527 A1 | 10/2005 | Slatkine | |
| 2005/0256515 A1 | 11/2005 | Anderson et al. | |
| 2006/0004306 A1 | 1/2006 | Altshuler et al. | |
| 2006/0004347 A1 | 1/2006 | Altshuler et al. | |
| 2006/0009749 A1 | 1/2006 | Weckwerth et al. | |
| 2006/0009750 A1 | 1/2006 | Altshuler et al. | |
| 2006/0013533 A1 | 1/2006 | Slatkine | |
| 2006/0020309 A1 | 1/2006 | Altshuler et al. | |
| 2006/0030908 A1 | 2/2006 | Powell et al. | |
| 2006/0074468 A1 | 4/2006 | Neev | |
| 2006/0129214 A1 | 6/2006 | Da Silva et al. | |
| 2006/0142750 A1 | 6/2006 | Da Silva et al. | |
| 2006/0224148 A1 | 10/2006 | Cho et al. | |
| 2006/0247609 A1 | 11/2006 | Mirkov et al. | |
| 2006/0253112 A1 | 11/2006 | Suarez et al. | |
| 2006/0259102 A1 | 11/2006 | Slatkine | |
| 2006/0265032 A1 | 11/2006 | Hennings et al. | |
| 2006/0293722 A1 | 12/2006 | Slatkine et al. | |
| 2008/0200908 A1* | 8/2008 | Domankevitz | 606/9 |

FOREIGN PATENT DOCUMENTS

| | | |
|---|---|---|
| CA | 2131750 | 1/1996 |
| DE | 195 12 481 | 10/1995 |
| EP | 0 142 671 | 5/1985 |
| EP | 0 292 621 | 11/1988 |
| EP | 0 348 862 | 1/1990 |
| EP | 0 575 274 | 12/1993 |
| EP | 0724866 A1 | 8/1996 |
| EP | 0763371 A2 | 3/1997 |
| GB | 2 123 287 | 2/1984 |
| GB | 2 336 545 | 10/1999 |
| JP | 63-249577 | 10/1988 |
| JP | 64-080309 | 3/1989 |
| JP | 03-193003 | 8/1991 |
| JP | 04-067860 | 3/1992 |
| JP | 04-322668 | 11/1992 |
| JP | 5-329218 | 12/1993 |
| WO | WO 84/02644 | 7/1984 |
| WO | WO 86/02783 | 5/1986 |
| WO | WO 89/00027 | 1/1989 |
| WO | WO 92/16338 | 10/1992 |
| WO | WO 92/19165 | 11/1992 |
| WO | WO 93/05920 | 4/1993 |
| WO | WO 95/15134 | 6/1995 |
| WO | WO 95/15725 | 6/1995 |
| WO | WO 97/37723 | 10/1997 |
| WO | WO 99/27863 | 6/1999 |
| WO | WO 0056240 A1 * | 9/2000 |
| WO | WO 02/35983 | 5/2002 |
| WO | WO 02/053050 | 7/2002 |
| WO | WO 02/087700 | 11/2002 |
| WO | WO 03/005921 | 1/2003 |
| WO | WO 2004/086947 | 10/2004 |
| WO | WO 2005/046793 | 5/2005 |

OTHER PUBLICATIONS

Mosby's Dental Dictionay, Acne, Elsevier Health Sciences, [Retrieved on Jun. 8, 2008]. Retrived from the INternet<URL: http://www.credoreference.com/emtry/ehsdent/acne>.*

Dorland's Illustrated Medical Dictionary, Rosacea, [Retrived on Jun. 8, 2009]. Retried from Internet<URL: http://www.xreferplus.com/entry/ehsdorland/rsacea>.*

Alster, T., "Laser Hair Removal: Are the Results Permanent?," *Laser Focus*, 21-23 (1993).

Anderson et al., "The Optics of Human Skin," *The Journal of Investigative Dermatology*, 77(1):13-19 (1981).

Anderson et al., "Lasers in Dermatology Provide a Model for Exploring New Applications in Surgical Oncology," *International Advances in Surgical Oncology*, 5:341-358 (1982).

Anderson et al., "Selective Photothermolysis: Precise Microsurgery by Selective Absorption of Pulsed Radiation," *Science*, 220:524-527 (1983).

Anderson, R., "Optics of the Skin," in *Clinical Photomedicine*, ed. Marcel Dekker Inc., New York, New York, 28-31 (1993).

Anderson et al., "Fractional Photothermolysis Redefines Facial Skin Regeneration Science," *Aesthetic Buyers Guide*, Mar./Apr. 2004.

Anvari et al., "Selective Cooling of Biological Tissues During Pulsed Laser Irradiation," Abstract 17, *American Society for Laser Medicine and Surgery*, Abstracts (1995).

Anvari et al., "Dynamic Epidermal Cooling in Conjunction with Laser Treatment of Port-Wine Stains: Theoretical and Preliminary Clinical Evaluations," *Lasers in Medical Science*, 10:105-112 (1995).

Anvari et al., "A Theoretical Study of the Thermal Response of Skin to Cryogen Spray Cooling and Pulsed Laser Irradiation: Implications for Treatment of Port Wine Stain Birthmarks," *Phys. Med. Biol.*, 40:1451-1465 (1995).

Anvari et al., "Selective Cooling of Biological Tissues: Application for Thermally Mediated Therapeutic Procedures," *Phys. Med. Biol.*, 40:241-252 (1995).

Awan, K., "Argon Laser Treatment of Trichiasis," *Ophthalmic Surgery*, 17(10):658-660 (1986).

Bartley et al., "An Experimental Study to Compare Methods of Eyelash Ablation," *Ophthalmology*, 94:1286-1289 (1987).

Berlien et al., "Lasers in Pediatric Surgery," *Progress in Pediatric Surgery*, 25:5-22 (1990).

Brunnberg, et al., "Evaluation of the Long Pulsed High Fluence Alexandrite Laser Therapy of Leg Telangiectasia," *Lasers in Surgery and Medicine*, 31:359-362 (2002).

Burton, C.S., "GentleLASE® Treatment of Café au Lait," Clinical Bulletin No. 7, Candela Corporation, 2 pages (Apr. 2003).

Campbell, D.C., "Thermoablation Treatment for Trichiasis Using the Argon Laser," *Australian and New Zealand Journal of Ophthalmology*, 18(4):427-430 (1990).

Cauger, D.M., "Analytical Report, Apogee Elite, Cynosure, Inc.," Laser & Light Technology, Aesthetic Trends & Technologies™ 3(4):6 pages (Summer 2004).

Crane, J.S., "GentleLASE® Treatment of Hyperpigmentation," Clinical Bulletin No. 6, Candela Corporation, 2 pages (Apr. 2003).

Crane, J.S., "GentleLASE® Treatment of Sun-Damaged Skin," Clinical Bulletin No. 13, Candela Corporation, 2 pages (Sep. 2004).

Dixon et al., "Argon and Neodymium YAG Laser Therapy of Dark Nodular Port Wine Stains in Older Patients," *Lasers in Surgery and Medicine*, 6:5-11 (1986).

Dover et al., "Pigmented Guinea Pig Skin Irradiated With Q-Switched Ruby Laser Pulses," *Arch. Dermatol.*, 125:43-49 (1989).

Dover et al., "Illustrated Cutaneous Laser Surgery," in *A Practioner's Guide*, ed. Appleton & Lange, Norwalk, Connecticut (1990).

Dover et al., "Laser Hair Removal," 1-6.

Eremia et al., "A Side-by-Side Comparative Study of 1064 nm Nd:YAG, 810 nm Diode and 755 nm Alexandrite Lasers for Treatment of 0.3-3 mm Leg Veins," *Dermatol. Surg.*, 28:224-230 (2002).

Eubanks, S.W., "Treatment of Solar Lentigines with GentleLASE® Long-Pulsed Alexandrite Laser," Clinical Bulletin No. 10, Candela Corporation, 2 pages (Nov. 2003).

Finkel et al., "Pulsed Alexandrite Laser Technology for Noninvasive Hair Removal," *Journal of Clinical Laser Medicine & Surgery*, 15(5):225-229 (1997).

Finkelstein et al., "Epilation of Hair-Bearing Urethral Grafts Using the Neodymium:YAG Surgical Laser," *The Journal of Urology*, 146:840-842 (1991).

Gilchrest et al., "Chilling Port Wine Stains Improves the Response to Argon Laser Therapy," *Plastic and Reconstructive Surgery*, 69(2):278-283 (1982).

Goldman et al., "Effect of the Laser Beam on the Skin: Preliminary Report," *The Journal of Investigative Dermatology*, 40:121-122 (1963).

Goldman et al., "Effect of the Laser Beam on the Skin: III. Exposure of Cytological Preparations," *The Journal of Investigative Dermatology*, 247-251 (1963).

Goldman et al., "Pathology of the Effect of the Laser Beam on the Skin," *Nature*, 197(4870):912-914 (1963).

Goldman et al., "The Biomedical Aspects of Lasers," *JAMA*, 188(3):230-234(1964).

Goldman et al., "Impact of the Laser on Nevi and Melanomas," *Archives of Dermatology*, 90:71-75(1964).

Goldman et al., "The Effect of Repeated Exposures to Laser Beams," *Acta Dermato-Venerologica*, 44:264-268 (1964).

Goldman et al., "Radiation From a Q-Switched Ruby Laser," *The Journal of Investigative Dermatology*, 69-71 (1964).

Goldman et al., "Treatment of Basal Cell Epithelioma by Laser Radiation," *JAMA*, 189(10):773-775 (1964).

Goldman, L., "Comparison of the Biomedical Effects of the Exposure to Low and High Energy Lasers," *Annals of New York Academy of Sciences*, 802-831 (1965).

Goldman, L., "Dermatologic Manifestations of Laser Radiation," Proceedings of the First Annual Conference on Biologic Effects of Laser Radiation, Federation of American Societies for Experimental Biology, Supp. No. 14:S-92-S-93 (Jan.-Feb. 1965).

Goldman et al., "Laser Action at the Cellular Level," *JAMA*, 198(6):641-644 (1966).

Goldman et al., "Investigative Studies With Quartz Rods for High Energy Laser Transmission," *Medical Research Engineering*, 12-17 (1967).

Goldman et al., "Laser Treatment of Tattoos," *JAMA*, 201(11):841-844 (1967).

Goldman et al., "Replica Microscopy and Scanning Electron Microscopy of Laser Impacts on the Skin," *The Journal of Investigative Dermatology*, 32(1):18-24 (1968).

Goldman et al., "Investigative Studies with the Laser in the Treatment from Basal Cell Epitheliomas," *Southern Medical Journal*, 61:735-742 (1968).

Goldman, L., "The Skin," *Arch. Environ. Health*, 18:434-436 (1969).

Goldman et al., "Preliminary Investigation of Fat Embolization for Pulsed Ruby Laser Impacts of Bone," *Nature*, 221:61-363 (1969).

Goldman et al., "Long-Term Laser Exposure of a Senile Freckle," *Arch. Environ Health*, 22:401-403 (1971).

Goldman et al., "The Laser in Dermatology," in *Lasers in Medicine*, ed. Gordon and Breach, New York, New York 329-352 (1971).

Goldman, L., "Effects of New Laser Systems on the Skin," *Arch. Dermatol.*, 108:385-390 (1973).

Goldman, L., "Laser Surgery for Skin Cancer," *New York State Journal of Medicine*, 1897-1900 (1977).

Goldman, L., "Surgery by Laser for Malignant Melanoma," *J. Dermatol. Surg. Oncol.*, 5(2):141-144 (1979).

Gossman et al., "Experimental Comparison of Laser and Cryosurgical Cilia Destruction," *Ophthalmic Surgery*, 23(3):179-182 (1992).

Gossman et al., "Prospective Evaluation of the Argon Laser in the Treatment of Tichiasis," *Ophthalmic Surgery*, 23(3):183-187 (1992).

Grekin et al., "Tin Ethyl Etiopupurin (SnET2): Phase I/II Clinical Results for the Treatment of Aids-Related Cutaneous Kaposi's Sarcomas at the University of California, San Francisco," Abstract 207, *American Society for Laser Medicine and Surgery*, Abstracts 44.

Grossman et al., "Damage to Hair Follicles by Normal-Mode Ruby Laser Pulses," *Journal of the American Academy of Dermatology*, 35:889-894 (1996).

Grossman et al., "PDT for Hirsutism," Abstract 205, *American Society for Laser Medicine and Surgery*, Abstracts 44.

Gustafsson et al., "A Variable Pulsewidth Vascular System for Dermatology," *SPIE*, 2128:188-196 (1994).

Haina et al., "Possibilities for the Increase of the Coagulation Depth in Skin with the Argonlaser," in *Waidelich W*, ed. Springer, Berlin-Heidelberg-New York-Tokyo (1987).

Haina et al., "Improvement of Therapy Results in Treatment of Port Wine Stains with the Argonlaser," in *Waidelich W*, eds. Springer, Berlin-Heidelberg-New York-Tokyo (1987).

Hellwig et al., "Treatment of Vascular Malformations and Benign Pigmented Lesions by Pulsed Dye Laser, Photoderm VL, and Q-Switched Ruby Laser,"(Abstract) *Laryngo-Rhino-Otol.*, 74:634-641 (1995).

Huerter et al., "Multiple Eruptive Vellus Hair Cysts Treated with Carbon Dioxide Laser Vaporization," *Journ. Dermatol. Surg. Oncol.*, 13(3):260-263 (1987).

Iwaki, K., "Treatment of Epidermal Pigmented Lesions With a Long-Pulsed Alexandrite Laser," Clinical Paper No. 2, Candela Corporation, 4 pages (Jun. 2003).

Iwasaki et al., "Development of Laser Systems for Treatment of Hyperpigmented Skin Lesions," *Japanese Journal of Medical Electronics and Biological Engineering*, 27:26-34 (1989).

Kauvar et al., "Pulsed Alexandrite Laser for Treatment of Leg Telangiectasia and Reticular Veins," *Arch. Dermatol.*, 136:1371-1375 (2000).

Khan et al., "Optical Clearing of In Vivo Human Skin: Implications for Light-Based Diagnostic Imaging and Therapeutics," *Lasers in Surgery and Medicine*, 34:83-85 (2004).

Khan et al., "Can Topically Applied Optical Clearing Agents Increase the Epidermal Damage Threshold and Enhance Therapeutic Efficacy?" *Lasers in Surgery and Medicine*, 35:93-95 (2004).

Kincade, K., "First Laser Hair-Removal System Gains FDA Clearance," *Laser Focus World* Jun. 1995.

Kincade, K., "New Procedures Push Tissue Studies Beneath the Surface," *Laser Focus World* Aug. 57-63 (1995).

Klein et al., "Biological Effects of Laser Radiation I: Threshold Studies and Reversible Depigmentation in Rodent Skin," *Nerem Record*, 108-109 (1965).

Kuhns et al., "Biological Effects of Laser Radiation II: Effects of Laser Irradiation on the Skin," *Nerem Record*, (1965).

Kuhns et al., "Laser Injury in Skin," *Laboratory Investigation*, 17(1):1-13 (1967).

Kuriloff, et al., "Pharyngoesophageal Hair Growth: The Role of Laser Epilation," *Case Reports*, 98(4):342-345 (1988).

Landthaler et al., "Neodymium-YAG Laser Therapy for Vascular Lesions," *Journal of the American Academy of Dermatology*, 14(1):107-117 (1986).

Landthaler et al. "Laser Treatment of Port Wine Stains," *Dermatologica: Letters to the Editor*, 175:156-160 (1987).

Laor et al., "The Pathology of Laser Irradiation of the Skin and Body Wall of the Mouse," *Laser Irradiation*, 47(4):643-663 (1965).

Lask et al., "Neodymium: Yttrium-Aluminum-Garnet Laser for the Treatment of Cutaneous Lesions," *Clinics in Dermatology*, 13:81-86 (1995).

Lask et al., "Nonablative Laser Treatment of Facial Rhytides," *SPIE*, 2970:338-349 (1997).

Lui et al., "Photodynamic Therapy of Malignant Skin Tumors with BPD Verteporfin (Benzoporphyrin Derivative)," Abstract 206, *American Society for Laser Medicine and Surgery*, Abstracts 44.

Maiman, T., "Biomedical Lasers Evolve Toward Clinical Applications," *Hospital Management*, 39-41 (1966).

Manstein et al., "Fractional Photothermolysis: A New Concept for Cutaneous Remodeling Using Microscopic Patterns of Thermal Injury," *Lasers in Surgery and Medicine*, 34:426-438 (2004).

Mansur, M.C., "GentleLASE® Treatment of Ephelides (Freckles)," Clinical Bulletin No. 8, Candela Corporation, 2 pages (Nov. 2003).

Margolls et al., "Visible Action Spectrum for Melanin-Specific Selective Photothermolysis," Lasers in Surgery and Medicine, 9:389-397 (1989).

Matsumoto, et al., "Ruby Laser Treatment of Melanin Pigmented Skin Lesions Using Toshiba Model LRT-301A Ruby Laser," Journal of Japanese Society for Laser Surgery and Medicine, 10(3):451-454 (1989).

McDaniel et al., "Laser Therapy of Spider Leg Veins: Clinical Evaluation of a New Long Pulsed Alexandrite Laser," Dermatol. Surg., 25:52-58 (1999).

Mehrabi, et al., "Use of the Alexandrite Laser for Treatment of Seborrheic Keratoses," Dermatol. Surg., 28:437-439 (2002).

Meloy, T., "The Laser's Bright Magic," National Geographic, 858-881(1966).

Mester et al., "Effect of Laser Beam on the Hair Growth of Mice," Experimental Medicine, 19:628-631 (1967).

Mester et al., "The Stimulating Effect of Low Power Laser-Rays on Biological Systems," Laser Review, 3-6 (1968).

Mester et al., "Effect of Laser Rays on Would Healing," The American Journal of Surgery, 122:532-535 (1971).

Mester et al., "The Biomedical Effects of Laser Application," Lasers in Surgery and Medicine, 5:31-39 (1985).

Milner et al., "Dynamic Cooling for Spatial Confinement of Laser Induced Thermal Damage in Collagen," Abstract 262, American Society for Laser Medicine and Surgery, Abstracts (1995).

Miyasaka et al., "Basic and Clinical Studies of Laser for Hyperpigmented Skin Lesions," Journal of the Japanese Society for Laser Surgery and Medicine, 11:117-127 (1991).

Nakaoka et al., "The Square and Uniform Intensity Ruby Laser for the Treatment of Pigmented Skin Lesions," European Journal of Plastic Surgery, 15:23-30 (1992).

Nelson et al., "Dynamic Cooling of the Epidermis During Laser Port Wine Stain Therapy," Abstract 253, American Society for Laser Medicine and Surgery, Abstracts (1994).

Nelson et al., "Epidermal Cooling During Pulsed Laser Treatment of Selected Dermatoses," SPIE, 2623:32-39 (1995).

Nelson et al., "Dynamic Epidermal Cooling During Pulsed Laser Treatment of Port-Wine Stain," Arch. Dermatol., 131:695-700 (1995).

Nelson et al., "Dynamic Epidermal Cooling in Conjunction with Laser-Induced Photothermolysis of Port Wine Stain Blood Vessels," Lasers in Surgery and Medicine, 19:224-229 (1996).

Ohshiro et al., "The Ruby and Argon Lasers in the Treatment of Naevi," Annals Academy of Medicine, 12(2):(1983).

Ohtsuka et al., "Histological Studies and Clinical Experiences of Ruby Laser Treatment," 107-115 (1991).

Oshry et al., "Argon Green Laser Photoepilation in the Treatment of Trachomatous Trichiasis," Ophthalmic Plastic and Reconstructive Surgery, 10(4):253-255 (1994).

Parlette et al., "Optimal Pulse Durations for the Treatment of Leg Telangiectasias With a Neodymium YAG Laser," Lasers in Surgery and Medicine, 9999:1-8 (2005).

Parrish et al., "Selective Thermal Effects with Pulsed Irradiation from Lasers: From Organ to Organelle," The Journal of Investigative Dermatology, 80(6):75s-80s (1983).

Polla et al., "Melanosomes Are a Primary Target of Q-Switched Ruby Laser Irradiation in Guinea Pig Skin," The Journal of Investigative Dermatology, 89(3):281-286 (1987).

Raulin et al., "Effective Treatment of Hypertrichosis with Pulsed Light: A Report of Two Cases," Ann. Plast. Surg., 39:169-174 (1997).

Riggle et al., "Laser Effects on Normal and Tumor Tissue," Laser Applications in Medicine and Biology, 1:35-65 (1971).

Rosenbach, A., "Treatment of Medium-Brown Solar Lentigines Using an Alexandrite Laser Designed for Hair Reduction," Arch. Dermatol., 138:547-548 (2002).

Rosenfeld et al., "Treatment of Cutaneous and Deep Vascular Lesions with the Nd:YAG Laser," Lasers in Surgery and Medicine, 6:20-23 (1986).

Rosenfeld et al., "The Treatment of Cutaneous Vascular Lesions with the ND:YAG Laser," Annals of Plastic Surgery, 21(3):223-230 (1988).

Ross et al., "Laser Treatment of Leg Veins: Physical Mechanisms and Theoretical Considerations," Lasers in Surgery and Medicine, 36:105-116 (2005).

Rostan, E.F., "Long Pulsed Alexandrite for the Treatment of Lentigines of the Face and Hands," Clinical Bulletin No. 12, Candela Corporation, 2 pages, (Aug. 2004).

Schirmer, K., "Simultaneous Thermal and Optical Breakdown Mode Dual Laser Action," Ophthalmologica, 205:169-177 (1992).

Shapshay et al., "Neodymium-YAG Laser Photocoagulation of Hemangiomas of the Head and Neck," Laryngoscope, 97:323-330 (1987).

Shimbashi et al., "Ruby Laser Treatment of Pigmented Skin Lesions," Aesthetic Plastic Surgery, 19:225-229 (1995).

Smartlipo: Laser Lipolysis With Pulsed Nd:YAG Laser Brochure, DEKA M.E.L.A. s.r.l., Italy, 2 pages.

Smoothbeam Brochure, Candela Corporation, 6 pages (2004).

Solomon et al., "Histopathology of the Laser Treatment of Port-Wine Lesions: Biopsy Studies of Treated Areas Observed up to Three Years After Laser Impacts," The Journal of Investigative Dermatology, 50(2):141-146 (1968).

Stewart, M., "Sebaceous Gland Lipids," Seminars in Dermatology, 11(2):100-105 (1992).

Svaasand et al., "Melanosomal Heating During Laser Induce Photothermolysis of Port Wine Stains," Abstract 233, American Society for Laser Medicine and Surgery, Abstracts (1995).

Svaasand et al., "Epidermal Heating During Laser Induced Photothermolysis of Port Wine Stains: Modeling Melanosomal Heating After Dynamic Cooling the Skin Surface," SPIE, 2323:366-377 (1994).

Takata et al., "Laser-Induced Thermal Damage of Skin," SAM-TR-77-38, USAF School of Aerospace Medicine (1977).

Tanino et al., "Development of Ruby Laser System for Medical Use," (Abstract) Journal of the Japanese Society for Laser Surgery and Medicine, 11(4):93-98 (1991).

Taylor et al., "Treatment of Tattoos by Q-Switched Ruby Laser," Arch. Dermatol., 126:893-899 (1990).

"Tech News: Lasers and Hair," Circle 21 (1983).

Tranner et al., "Photodynamic Synovectomy with Benzoporphyrin Derviative in a Rabbit Model of Rheumatoid Arthritis," Abstract 204, American Society for Laser Medicine and Surgery, Abstracts 44.

Tri-Active Brochure, DEKA M.E.L.A. s.r.l., Italy, 4 pages.

Tsai et al., "Near-infrared Absorption Property of Biological Soft Tissue Constituents," Journal of Medical and Biological Engineering, 21(1):7-14 (2001).

van Gemert et al., "Is There an Optimal Laser Treatment for Port Wine Stains?," Lasers Surg. Med., 6:76-83 (1986).

van Gemert et al., "Limitations of Carbon Dioxide Lasers for Treatment of Port Wine Stains," Arch. Derm., 123:71-73 (1987).

van Gemert et al., "Temperature Behavior of a Model Port-Wine Stain During Argon Laser Coagulation," Phys. Med. Biol., 27(9):1089-1104 (1982).

Waldman et al., "Cutaneous Inflammation: Effects of Hydroxy Acids and Eicosanoid Inhibitors on Vascular Permeability," Abstracts 523, 88(4):(1987).

Wang et al., "Characterization of Human Scalp Hairs by Optical Low-Coherence Reflectometry," Optics Letters, 20(6):524-526 (1995).

Warren et al., "Pigmentation Induction by Melanocyte Stimulating Hormone in Human Skin Culture," Abstracts 523, 88(4):(1987).

Wastek et al., "Characterization of H-Substance P (SP) Binding to a Mouse Monoclonal Mast Cell Line (MC/9)," Abstracts 523, 88(4):(1987).

Watanabe et al., "The Effect of Pulse Duration on Selective Pigmented Cell Injury by Dye Lasers," Abstracts 523, 88(4):(1987).

Watanabe et al., "Comparative Studies of Femtosecond to Microsecond Laser Pulses on Selective Pigmented Cell Injury in Skin," Photochemistry and Photobiology, 53(6):757-761 (1991).

Weissman et al., "Growth, Collagen and Glycosaminoglcan Synthesis by Dermal Fibroblasts Derived From Puva Treated and Psoriatic Patients," Abstracts 523, 88(4):(1987).

Welch et al., "Evaluation of Cooling Techniques for the Protection of the Epidermis During Nd:YAG Laser Irradiation of Skin," in Neodymium-YAG Laser in *Medicine and Surgery*, ed. SN Joffe, Elsevier, New York, 196-204 (1983).

Werse et al., "Effects of Essential Fatty Acid Deficiency on the Structure and Function of Epidermal Lipids," Abstracts 523, 88(4):(1987).

"Workshop on Analysis of Laser-Tissue Interaction for Clinical Treatment," University of Texas, Austin, TX 78712, Jul. 14-18, 1986.

Yules et al., "The Effect of Q-Switched Ruby Laser Radiation on Dermal Tattoo Pigment in Man," *Arch. Surg.*, 95:179-180 (1967).

Zeitler et al., "Laser Characteristics that Might be Useful in Biology," *Laser Applications in Medicine and Biology*, 1:1-18 (1971).

"The Apogee Elite™ Two-in-One Laser System—Innovative from Cynosure," The Cynosure Apogee Elite Laser System Brochure, Candela Corporation, 3 pages (2004).

"The Apogee 5500™—For the Removal of Hair and Pigmented Lesions," The Cynosure Apogee 5500 Alexandrite Laser Brochure, Candela Corporation, 3 pages (2004).

"The Alexandrite Laser System for Effective Hair Removal," Anion Brochure, WaveLight Laser Technologies AG, 4 pages.

\* cited by examiner

FIG. 2

METHODS FOR TREATING PIGMENTARY AND VASCULAR ABNORMALITIES IN A DERMAL REGION

CROSS-REFERENCE TO RELATED APPLICATION

This application claims the benefit of and priority to U.S. provisional patent application No. 60/753,821 filed Dec. 23, 2006, which is owned by the assignee of the instant application and the disclosure of which is incorporated herein by reference in its entirety.

FIELD OF THE INVENTION

The invention relates generally to using a beam of radiation to treat dermatological conditions, lesions, or disorders, and more particularly to treating pigmented lesions and vascular lesions using an alexandrite laser.

BACKGROUND OF THE INVENTION

Non-ablative laser/light treatments, e.g., facial photo rejuvenation, are becoming an increasingly popular procedure in correcting the undesired side effects of photo and chronological aging. Non-ablative facial treatments have been shown to improve rhytides, pilosebaceous changes, pigmentary skin alterations, lentigines, and vascular lesions including facial telangiectasias and diffuse redness. These treatments are attractive to physicians and patients because of minimal or no healing time and because they reduce inconvenience and risk for a patient.

Intense Pulsed Light (IPL) devices can be used for Type-I photo rejuvenation. This includes vascular (reds) and pigmentary (brown) changes associated with photoaging, lentigens, telangiectasia and symptoms of rosacea. An advantage of the IPL is that it can reduce both vascular and pigment dyschromias with one pass (e.g., using the same treatment parameters). This leads to ease of use, simplicity and speed of operation. A KTP 532 nm laser device with 10 mm spot is also capable of treating vascular and pigmentary changes in one pass. A disadvantage of a KTP device is that it is not well-suited for hair removal and other dermatological treatments. The IPL is not well-optimized for hair removal.

Alexandrite lasers are mainly known for their ability to remove hair. Recently, it has also been used for treating pigmented lesions. Dr. Rosenbach has used the alexandrite laser to treat medium-brown solar lentigines with fluences ranging from 35 to 50 J/cm$^2$ and a pulse duration of 5 msec (Arch. Dermatol., Vol. 138, April 2000, pp. 547-548). Dr. Mehrabi reported treatment of seborrheic keratoses using 100 J/cm$^2$ with a spotsize of 8 mm. Dr. Mehrabi's treatment shows that using high fluence with short pulse durations results in various unwanted side effects, such as scarring and hypopigmentation complications ("Lasers for Seborrheic Keratoses," Dermatol. Surg., Vol. 28, May 2002, pp. 437-439). Cynosure Laser Company markets an alexandrite laser for pigmented lesions and recommends using a customized short pulse mode (0.5 msec) to provide effective treatment of pigmented lesions. Candela Corporation has published several clinical papers and clinical bulletins regarding treatment of epidermal pigmented lesions with a 3 msec pulsed alexandrite laser (e.g., the GentleLase model laser). These treatments were performed with and without DCD cooling, and used fluences as high as 40 J/cm$^2$.

A disadvantage of using fluences less than 50 J/cm$^2$ for treating facial epidermal pigmented lesions such as lentigines is that they are not optimal for treating vascular lesions, and therefore, using the alexandrite laser with these treatment parameters cannot be useful for a single pass non-ablative skin treatment, where vascular lesions are present.

The alexandrite laser has also been used to treat vascular lesions. Dr. Kauvar used the 755 nm, 3 msec alexandrite laser with an 8 mm spot and fluences of 60 to 80 J/cm$^2$ to treat leg telangiectasia and reticular veins ("Pulsed Alexandrite Laser for the Treatment of Leg Telangiectasia and Reticular Veins," Arch Dermatol, Vol. 36, November 2000, pp. 1371-1375). Although vessel clearance was good, hyperpigmentation developed in 35% of treatment sites. Dr. Eremia compared side by side 1064 nm, 810 nm, and 755 nm for the treatment of leg veins ("A Side-by-Side Comparative study of 1064 nm Nd:YAG, 810 nm Diode and 755 nm Alexandrite Lasers for Treatment of 0.3-3 mm Leg Veins," Dernatol. Surg. 28:3 March 2002, pp. 224-230). Dr. Eremia used 3 msec pulse duration with fluences of 60-70 J/cm$^2$ and a spot with 8 mm. Dr. Eremia claims that lower fluences do not consistently damage leg veins. Lowering the fluences below 50-60 J/cm$^2$ drastically reduces the effectiveness for leg veins.

A disadvantage of using these pulse durations for treating vascular lesions is that, for example, they are associated with higher occurrence of side effects such as purpura and post-inflammatory hyperpigmentation. In addition, these studies examined leg veins only, and not facial vascular lesions. Therefore, using an alexandrite laser with these treatment parameters may not be useful for a single pass non-ablative skin treatment. In facial rejuvenation treatments, it is desirable to have minimum side effects.

The Arion laser device is a long-pulsed alexandrite laser system. The main area of application is laser epilation. The system is also suitable for the treatment of superficial vascular alterations. The laser can produce up to 100 J/cm$^2$, a pulse width of 1-50 msec, and spot sizes of 3, 4, and 5 mm. The system generally uses air cooling.

There are also several patents on using the alexandrite laser for the treatment of vascular lesions, e.g., U.S. Pat. Nos. 5,749,868; 5,843,072; 6,273,883; and 6,610,052. These patents disclose methods and devices to selectively damage vascular targets and blood vessels (leg veins, telangiectasia, ecstatic blood vessels of vascular lesions, and port wine stains below the dermal/epidermal boundary), as well as other biological tissue. Fluences up to about 50 J/cm$^2$ are reported.

A disadvantage of the methods described in these patents is that they are not optimal for treating vascular lesions. In addition, the fluences used by these methods do not lead to effective vessel closure for a vascular treatment, and the treatments do not include cooling of the skin. The 755 nm is strongly absorbed by melanin within the epidermis, and therefore epidermal cooling is important. Optimal vascular treatments cannot be performed using the best modes of operation suggested by the above patents and patent applications.

Therefore, what is needed is an improved method and apparatus based on a 755 nm alexandrite laser system, or similar wavelength device, that can perform non-ablative treatments targeting pigmentary (browns) and vascular (reds) abnormalities using a single pass of the device.

SUMMARY OF THE INVENTION

The invention, in one embodiment, features a method and apparatus for treating dermatological conditions. For example, a system can be used for skin photo rejuvenation, e.g., non-ablative skin treatments. Skin photo rejuvenation can be accomplished with a 755 nm alexandrite laser system with a single pass, e.g., treating pigmentary (browns) and vascular (reds) abnormalities with the same treatment parameters. For example, one or more pigmentary abnormalities and one or more vascular abnormalities in a target skin region can be treated without the need to change the handpiece and/or beam parameters. The system can be used for skin photo rejuvenation of the face.

Development of an effective treatment for vascular and pigmentary abnormalities using a single pass enables a single device to be used for a treatment. This provides a simpler and faster treatment since separate treatment passes or separate devices do not have to be used to treat both indications. In addition, alexandrite lasers, e.g., a GentleLase model laser available from Candela Corporation (Wayland, Mass.), are widely recognized as providing the best laser means for hair removal treatments. The development of an effective treatment for vascular and pigmentary abnormalities using an alexandrite laser enables a universal laser system to be developed. For example, a single device can be used to treat many common dermatologic conditions, including unwanted hair, vascular abnormalities, and pigmentary abnormalities. This is advantageous for a doctor administering treatment because he/she needs to purchase only a single device. It is advantageous to a patient because they can have multiple symptoms/indications treated with a single laser pulse. Having a single set of parameters that can be used to treat at least vascular abnormalities and pigmentary abnormalities can also reduce the cost of a treatment and the time needed for a treatment.

In one aspect, there is a method of treating a dermatological condition in a target region of skin. A beam of radiation is provided. The beam of radiation has a wavelength between about 700 nm and about 800 nm, a fluence greater than about 50 $J/cm^2$, and a pulse duration between about 10 msec and about 300 msec. The beam of radiation is delivered to the target region of skin to affect (i) at least one pigmentary abnormality disposed in an epidermal region of the target region and (ii) at least one vascular abnormality disposed in a dermal region of the target region. A surface of the epidermal region of the target region of skin is cooled to prevent substantial unwanted injury to at least a portion of the epidermal region.

In another aspect, there is a method of treating a dermatological condition in a target region of skin. A beam of radiation is provided. The beam of radiation has a wavelength between about 700 nm and about 800 nm, a fluence of between about 80 $J/cm^2$ and about 100 $J/cm^2$, and a pulse duration between about 20 msec and about 60 msec. The beam of radiation is delivered to the target region of skin to affect (i) at least one pigmentary abnormality disposed in an epidermal region of the target region and (ii) at least one vascular abnormality disposed in a dermal region of the target region. A surface of the epidermal region of the target region of skin is cooled to prevent substantial unwanted injury to at least a portion of the epidermal region.

In still another aspect, there is a method of treating a dermatological condition disposed on a patient's face. A beam of radiation is provided. The beam of radiation has a wavelength between about 700 nm and about 800 nm, a fluence of between about 80 $J/cm^2$ and about 100 $J/cm^2$, and a pulse duration between about 20 msec and about 60 msec. The beam of radiation is delivered to the beam of radiation to a target region of skin of the patient's face to affect (i) at least one pigmentary abnormality disposed in an epidermal region of the target region and (ii) at least one vascular abnormality disposed in a dermal region of the target region. A surface of the epidermal region of the target region of skin is cooled to prevent substantial unwanted injury to at least a portion of the epidermal region.

In other examples, any of the aspects above, or any apparatus or method described herein, can include one or more of the following features. A dynamic cooling device can be used to cool the epidermal region of the target region of skin. In certain embodiments, a portion of the dermal region can be cooled. The portion of the epidermal region protected can overlie a pigmentary abnormality and/or a vascular abnormality. The target region of skin can be disposed on a patient's face (e.g., for a treatment of facial telangiectasia).

A delivery device can direct the beam of radiation to the target region of skin. The delivery device can be positioned over the target region of skin. The delivery device can treat at least one vascular abnormality and at least one pigmentary abnormality while the delivery device is traversed across the surface of the target region of skin. In certain embodiments, a vascular abnormality and/or a pigmentary abnormality can be treated during a single pass of the delivery device.

In various embodiments, the beam of radiation can have a fluence of between about 60 $J/cm^2$ and about 300 $J/cm^2$. In some embodiments, the beam of radiation can have a fluence of between about 60 $J/cm^2$ and about 150 $J/cm^2$. In certain embodiments, the beam of radiation can have a fluence of between about 80 $J/cm^2$ and about 100 $J/cm^2$. In various embodiments, the beam of radiation can have a wavelength of about 755 nm. The source of the beam of radiation can be an alexandrite laser. The pulse duration can be between about 20 msec and about 60 msec.

The beam of radiation can have a wavelength of about 755 nm, a fluence of between about 80 $J/cm^2$ and about 100 $J/cm^2$, and a pulse duration between about 20 msec and about 60 msec. The beam of radiation can have a fluence greater than about 100 $J/cm^2$ and a spotsize less than about 5 mm, and the beam of radiation can be used to treat a blood vessel.

Other aspects and advantages of the invention will become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

A beam of radiation can be provided to treat a dermatological condition in a target region of skin. The beam of radiation can be delivered to affect at least one pigmentary abnormality (e.g., a brown) and at least one vascular abnormality (e.g., a red) in the target region. By proper selection of beam parameters, a reduction of the pigmentary and vascular abnormalities can occur with minimal side effects (e.g., unintended epidermal damage, crusting, purpura, and/or pain). In addition, the abnormalities can be treated without the need to change the handpiece and/or beam parameters.

In certain embodiments, the beam of radiation can be delivered to the target region of skin to affect (i) at least one pigmentary abnormality disposed in an epidermal region of the target region and (ii) at least one vascular abnormality disposed in a dermal region of the target region. A surface of the epidermal region of the target region of skin can be cooled to prevent substantial unwanted injury to at least a portion of the epidermal region. A portion of the dermal region can be protected as well by cooling of the skin region.

A treatment can be within the class of treatments known as skin photo rejuvenation, e.g., a non-ablative skin treatments. Skin photo rejuvenation can be accomplished with a 755 nm alexandrite laser system with a single pass. For example, a pigmentary abnormality and a vascular abnormality can be treated using the same beam parameters. In various embodiments, the target area of skin can be disposed on a face, neck, or hand of a patient. In one embodiment, leg veins are treated. In addition, although the embodiments are described primarily in the context of pigmented lesions and vascular lesions, other dermatological conditions, lesions, and/or disorders can be treated using the invention. For example, treatments of hair, acne, wrinkles, skin laxity, fat and cellulite are contemplated by the invention.

Figure 1:
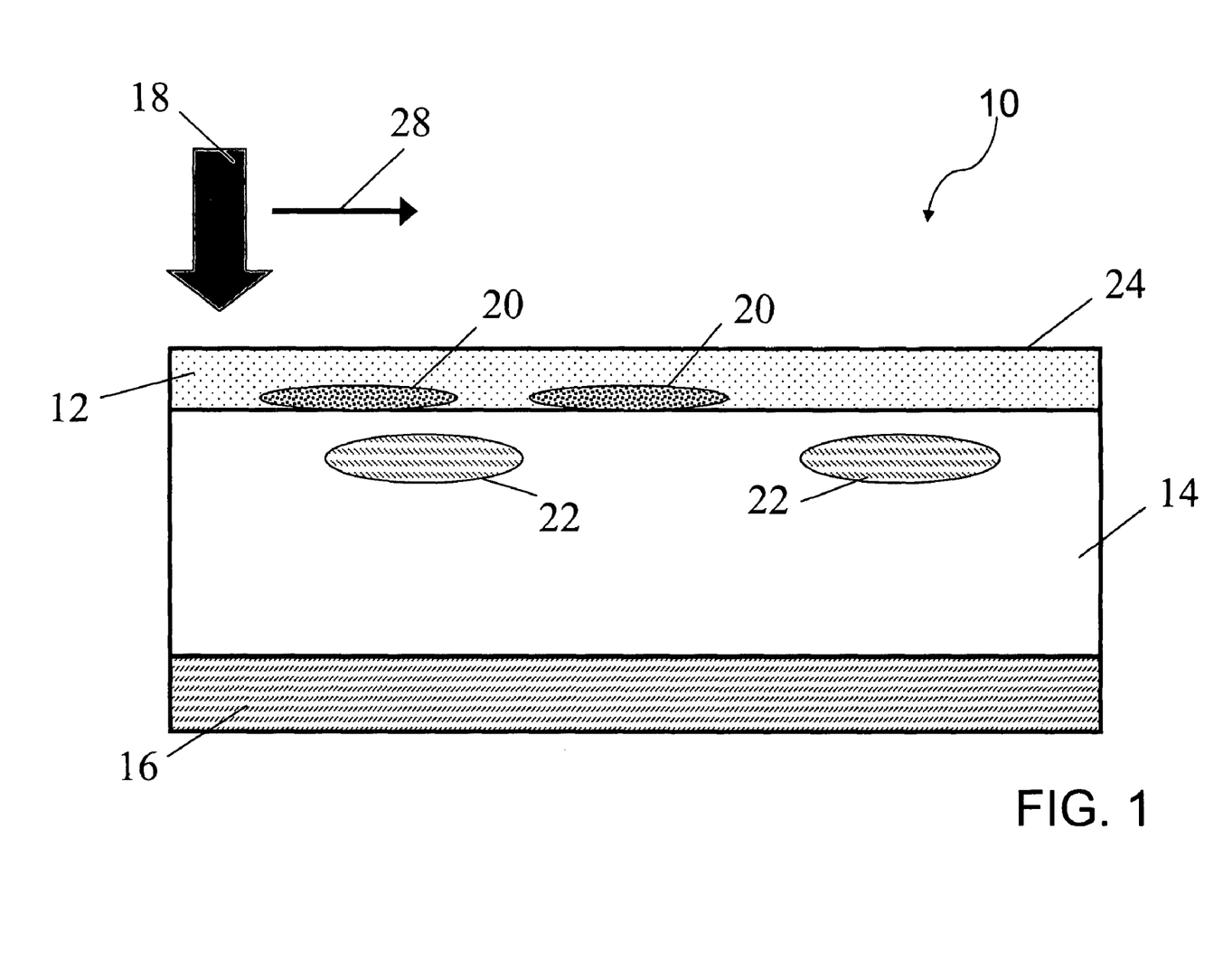
FIG. 1 shows a sectional view of skin that can be targeted with a beam of radiation.

FIG. 1 shows a target region of skin 10 including an epidermal region 12, a dermal region 14, and a layer of fatty tissue 16. A beam of radiation 18 can be used to treat at least a portion of the target region of skin 10. The target region can include at least one pigmentary abnormality 20 disposed in the epidermal region 12 and at least one vascular abnormality 22 disposed in the dermal region 14. The surface 24 of the epidermal region 12 can be cooled to protect at least a portion of the epidermal region 12 and/or the dermal region 14. The beam of radiation 18 can be traversed (28) along the surface 24 of the skin to perform a treatment.

The target region of skin 10 can include a pigmentary abnormality overlying a vascular abnormality. The target region of skin 10 can include a vascular abnormality overlying a pigmentary abnormality. The target region of skin 10 can include a pigmentary abnormality adjacent a pigmentary abnormality. In certain embodiments, a pigmentary abnormality can be partially or completely laterally displaced in relation to the vascular abnormality so that there is minimal or no overlap between the two.

In some embodiments, a plurality of pigmentary abnormalities and/or a plurality of vascular abnormalities can be treated within a single beam diameter. For example, using larger beam sizes, several blood vessels can be treated.

In some embodiments, the beam of radiation can be delivered to the target area to thermally injure, damage and/or destroy at least one pigmented abnormality and/or at least one vascular abnormality. Suitable target chromophores include, but are not limited to, melanin, melanin containing tissue, blood, hemoglobin, oxyhemoglobin, methemoglobin and blood containing tissue.

Vascular abnormalities that can be treated include, but are not limited to, leg veins, facial and leg telangiectasias, ecstatic blood vessels of vascular lesions, port wine stains diffused redness, and rosecea. Pigmentary abnormalities that can be treated include, but are not limited to, lentigines, freckles, and small flat seborrheic keratosis. The vascular abnormality can be treated in a dermal region of the target area of skin. The pigmentary abnormality can be treated in an epidermal region of the target area of skin. In some embodiments, the pigmentary abnormality treated can cross the dermal junction and a portion of the pigmentary abnormality can be in the dermal region.

In various embodiments, tissue in the target region can be heated to a temperature of between about 50° C. and about 100° C., although higher and lower temperatures can be used depending on the application. In one embodiment, the temperature is between about 55° C. and about 70° C. In one embodiment, the temperature is between about 70° C. and about 100° C.

In certain embodiments, a treatment can cause sufficient thermal injury in the dermal region of the skin to elicit a healing response to cause the skin to remodel itself. This can result in more youthful looking skin and an improvement in the appearance of cellulite. In one embodiment, sufficient thermal injury induces fibrosis of the dermal layer, fibrosis on a subcutaneous fat region, or fibrosis in or proximate to the dermal interface. In one embodiment, the treatment radiation can partially denature collagen fibers in the target region. Partially denaturing collagen in the dermis can induce and/or accelerate collagen synthesis by fibroblasts. For example, causing selective thermal injury to the dermis can activate fibroblasts, which can deposit increased amounts of extracellular matrix constituents (e.g., collagen and glycosaminoglycans) that can, at least partially, rejuvenate the skin. The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, and/or reduce discoloration of the skin.

Figure 2:
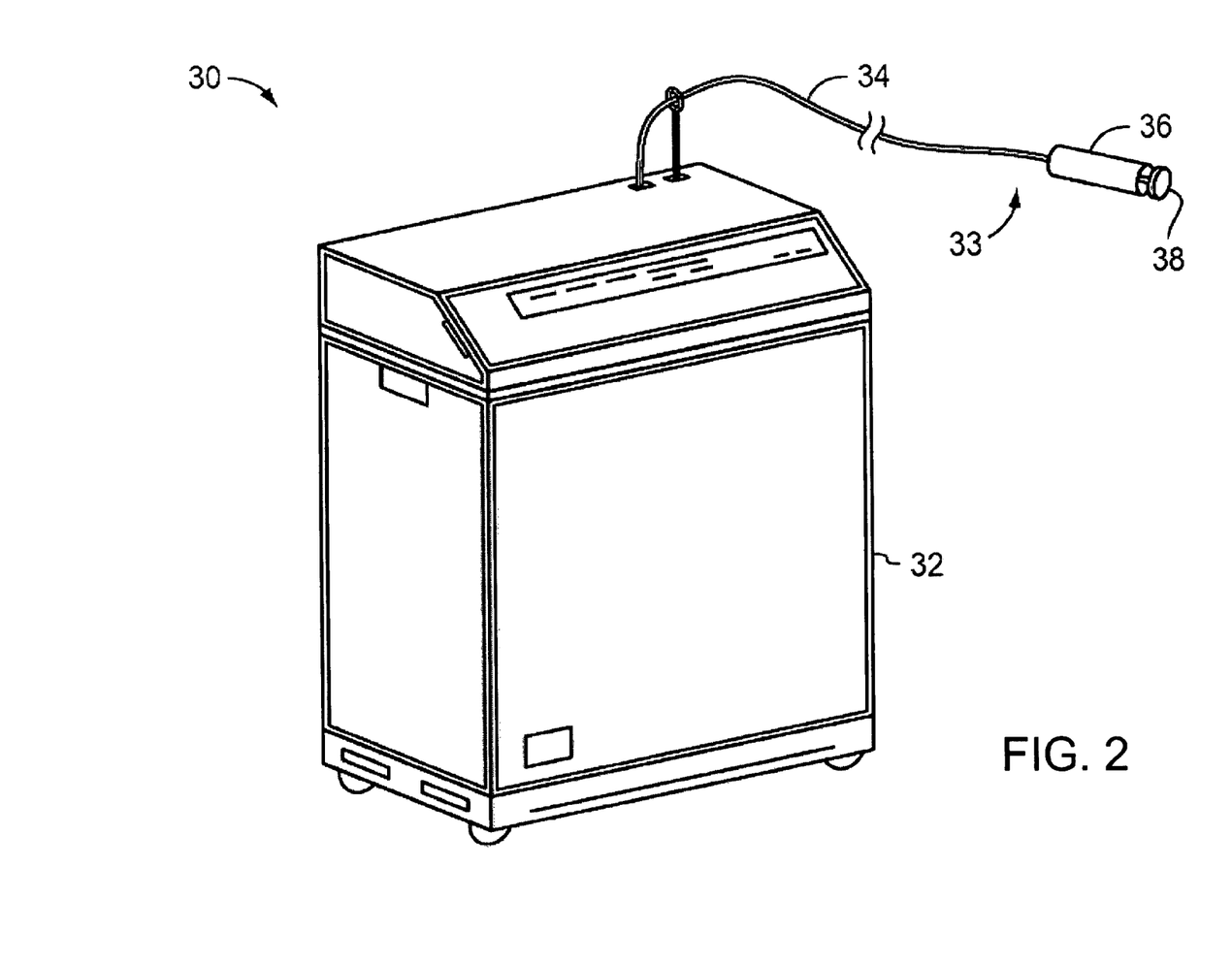
FIG. 2 shows an exemplary system for performing a treatment.

FIG. 2 shows an exemplary embodiment of a system 30 for treating tissue. The system 30 can be used to non-invasively deliver a beam of radiation to a target region. For example, the beam of radiation can be delivered through an external surface of skin over the target region. The system 30 includes an energy source 32 and a delivery system 33. In one embodiment, a beam of radiation provided by the energy source 32 is directed via the delivery system 33 to a target region. In the illustrated embodiment, the delivery system 33 includes a fiber 34 having a circular cross-section and a handpiece 36. A beam of radiation can be delivered by the fiber 34 to the handpiece 36, which can include an optical system (e.g., an optic or system of optics) to direct the beam of radiation to the target region. A user can hold or manipulate the handpiece 36 to irradiate the target region. The delivery system 33 can be positioned in contact with a skin surface, can be positioned adjacent a skin surface, can be positioned proximate a skin surface, can be positioned spaced from a skin surface, or a combination of the aforementioned. In the embodiment shown, the delivery system 33 includes a spacer 38 to space the delivery system 33 from the skin surface. In one embodiment, the spacer 38 can be a distance gauge, which can aid a practitioner with placement of the delivery system 33.

To minimize unwanted thermal injury to tissue not targeted (e.g., an exposed surface of the target region and/or the epidermal layer), the delivery system 33 shown in FIG. 2 can include a cooling system for cooling before, during or after delivery of radiation, or a combination of the aforementioned. Cooling can include contact conduction cooling, evaporative spray cooling, convective air flow cooling, or a combination of the aforementioned. In various embodiments, the apparatus can maintain the temperature of a surface or an upper portion of the skin between about −15° C. and about 30° C.

In one embodiment, the handpiece 36 includes a skin contacting portion that can be brought into contact with the skin. The skin contacting portion can include a sapphire or glass window and a fluid passage containing a cooling fluid. The cooling fluid can be a fluorocarbon type cooling fluid, which can be transparent to the radiation used. The cooling fluid can circulate through the fluid passage and past the window to cool the skin.

A spray cooling device can use cryogen, water, or air as a coolant. In one embodiment, a dynamic cooling device can be used to cool the skin (e.g., a DCD available from Candela Corporation). For example, the delivery system 33 shown in FIG. 2 can include tubing for delivering a cooling fluid to the handpiece 36. The tubing can be connected to a container of a low boiling point fluid, and the handpiece can include a valve for delivering a spurt of the fluid to the skin. Heat can be extracted from the skin by virtue of evaporative cooling of the low boiling point fluid. The fluid can be a non-toxic substance with high vapor pressure at normal body temperature, such as a Freon, tetrafluoroethane, or liquefied $CO_2$.

The time duration of cooling and of radiation application can be adjusted to maximize heating and thermal injury to the region proximate to the dermal interface. In tissue where the dermal interface is deeply situated, the cooling time can be lengthened such that cooling can be extended deeper into the skin. At the same time, the time duration of radiation application can be lengthened such that heat generated by the radiation in the region of dermis closer to the skin surface can be removed via thermal conduction and blood flow, thereby minimizing injury to the tissue overlying the dermal interface. Similarly if the dermis overlying the dermal interface is thin, the time duration of cooling and of radiation application can be adjusted to be shorter, such that thermal injury is confined to the region proximate to the dermal interface.

The beam of radiation can have a wavelength between about 700 nm and about 800 nm. In some embodiments, the beam of radiation has a wavelength of about 755 nm. The source of the beam of radiation can be an alexandrite laser. In one embodiment, the source of the beam of radiation is a variable pulsed duration alexandrite laser.

Because alexandrite laser light is highly absorbed by melanin and vessel closure typically requires higher fluence levels, dynamic cooling can be provide an effective treatment since dynamic cooling can extract heat from the skin efficiently. Furthermore, in the prior art, surface cooling is not always used when treating epidermal pigmented lesions because cooling can reduce a light source's effect on the pigment. Using dynamic cooling, cooling can protect the surface of the skin and higher fluences can be used to treat the pigmentary abnormality and the vascular abnormality simultaneously or substantially simultaneously.

In various embodiments, the beam of radiation can have a fluence up to about 500 $J/cm^2$. In one embodiment, the beam of radiation has a fluence of between about 60 $J/cm^2$ and about 300 $J/cm^2$, although higher and lower fluences can be used depending on the application. In one embodiment, the beam of radiation has a fluence of between about 60 $J/cm^2$ and about 150 $J/cm^2$. In one embodiment, the beam of radiation has a fluence between about 80 $J/cm^2$ and about 100 $J/cm^2$. High fluences can lead to better collagen shrinkage in a blood vessel wall and/or perivascular, and therefore better stenosis.

In various embodiments, beam of radiation can have a spotsize between about 0.5 mm and about 25 mm, although larger and smaller spotsizes can be used depending on the application. In one embodiment, the beam of radiation has a spotsize of between about 5 mm and about 10 mm. In one embodiment, the beam of radiation has a spotsize of between about 6 mm and about 8 mm. In one embodiment, the beam of radiation has a spotsize of about 6 mm. In certain embodiments, the beam of radiation has a spotsize of between about 1 mm and about 5 mm. For example, for spotsizes up to 5 mm, a fluence of between 100-500 $J/cm^2$ can be used. For spotsizes greater than 5 mm, a fluence of between 80-100 $J/cm^2$ can be used.

In certain embodiments, the beam of radiation can have a fluence greater than about 100 $J/cm^2$. For example, the beam of radiation can have a fluence of between about 120 $J/cm^2$ and about 500 $J/cm^2$. With smaller spotsizes, higher fluences can result in optimum collagen shrinkage and vessel contraction. In one embodiment, a fluence greater than 100 J/cm , and a spotsize of less than 5 mm (e.g., between 1 mm and 3 mm) is used to treat blood vessels having a diameter of between about 50 µm and about 1.5 mm.

In various embodiments, the beam of radiation can have a pulse duration between about 10 msec and about 300 msec, although a longer and shorter pulse duration can be used depending on the application. In one embodiment, the beam of radiation has a pulse duration between about 20 msec and about 100 msec. In one embodiment, the beam of radiation has a pulse duration between about 20 msec and about 60 msec. In one embodiment, the beam of radiation has a pulse duration between about 20 msec and about 40 msec. In one embodiment, the beam of radiation has a pulse duration between about 40 msec and about 60 msec. In one embodiment, the beam of radiation has a pulse duration of about 40 msec. In one embodiment, the beam of radiation has a pulse duration greater than about 40 msec.

In various embodiments, the beam of radiation can be delivered at a rate of between about 0.1 pulse per second and about 10 pulses per second, although faster and slower pulse rates can be used depending on the application.

In various embodiments, the parameters of the radiation can be selected to deliver the beam of radiation to a predetermined depth. In some embodiments, the beam of radiation can be delivered to the target area up to about 10 mm below a surface of the skin although shallower or deeper depths can be selected depending on the application. In some embodiments, the beam of radiation can be delivered to the target area up to about 5 mm below a surface of the skin. In some embodiments, the beam of radiation can be delivered to the target area up to about 4 mm below a surface of the skin. In some embodiments, the beam of radiation can be delivered to the target area up to about 2 mm below a surface of the skin. In some embodiments, the beam of radiation can be delivered to the target area up to about 1 mm below a surface of the skin.

Example Treatment

A variable pulsewidth alexandrite laser was used for facial skin rejuvenation. 15 patients with telangiectasias, facial redness, and/or pigmented lesions were treated with a long pulsed alexandrite laser equipped with a 6-mm spot and a dynamic cooling device (DCD). A pulse duration of 40 ms resulted in the greatest reduction in vascular and pigmented lesions with the least side effects. Once the optimal pulse duration and fluences were determined in a series of test sites, treatment was carried out 3 weeks later in a larger area. The final follow-up was three months after treatment.

Depending on the fluence level used, pulse durations shorter than 40 msec can cause purpura and unintended epidermal damage, and longer pulse durations are not as effective. During the treatment protocol, larger and bluer telangiectasias (>0.4 mm) tended to respond better than smaller ones. Darker lentigos responded better than lighter ones. Typical threshold fluences for simultaneous vascular and pigment reduction ranged from 80-95 $J/cm^2$. Pain was modest and was reduced by the addition of 4% lidocaine cream one hour prior to irradiation. One treatment session resulted in a mean vascular and pigment reduction of 30% and 50%, respectively. Side effects included crusting and purpura. Crusting was associated with darker skinned patients, shorter pulse durations, and shorter cooling times (with the DCD). In untanned skin types I-III, a variable pulsewidth alexandrite laser can be "tuned" for safe one-pass reduction of red and brown lesions on the face.

While the invention has been particularly shown and described with reference to specific illustrative embodiments, it should be understood that various changes in form and detail may be made without departing from the spirit and scope of the invention.

What is claimed:

1. A method of treating a pigmentary abnormality disposed in an epidermal region and a vascular abnormality disposed in a dermal region of a target region of skin, comprising:
   providing a beam of radiation having a wavelength between about 700 nm and about 800 nm, a fluence greater than about 50 J/cm$^2$, and a pulse duration between about 10 msec and about 300 msec;
   delivering, during a single pass of a delivery device, the beam of radiation to the target region of skin to affect (i) at least one pigmentary abnormality disposed in the epidermal region of the target region and (ii) at least one vascular abnormality disposed in the dermal region of the target region; and
   cooling a surface of the epidermal region of the target region of skin.

2. The method of claim 1 further comprising providing a dynamic cooling device to cool the epidermal region of the target region of skin.

3. The method of claim 1 wherein at least one pigmentary abnormality and at least one vascular abnormality are treated substantially simultaneously.

4. The method of claim 1 further comprising positioning, over the target region of skin, a delivery device capable of directing the beam of radiation to the target region of skin.

5. The method of claim 4 further comprising traversing the beam of radiation along the surface of the target region of skin to treat the at least one vascular abnormality and the at least one pigmentary abnormality during a single pass of the delivery device.

6. The method of claim 1 wherein the beam of radiation has a fluence of between about 60 J/cm$^2$ and about 300 J/cm$^2$.

7. The method of claim 1 wherein the beam of radiation has a fluence of between about 60 J/cm$^2$ and about 150 J/cm$^2$.

8. The method of claim 1 wherein the beam of radiation has a fluence of between about 80 J/cm$^2$ and about 100 J/cm$^2$.

9. The method of claim 1 wherein the beam of radiation has a wavelength of about 755 nm.

10. The method of claim 1 wherein the beam of radiation has a pulse duration between about 20 msec and about 60 msec.

11. The method of claim 1 wherein the beam of radiation has a wavelength of about 755 nm, a fluence of between about 80 J/cm$^2$ and about 100 J/cm$^2$, and a pulse duration between about 20 msec and about 60 msec.

12. The method of claim 1 wherein the vascular abnormality includes a blood vessel having a diameter of less than about 1.5 mm, the fluence is greater than about 100 J/cm$^2$, and the spotsize is less than about 5 mm.

13. The method of claim 1 wherein the target region of skin is disposed on a patient's face.

14. The method of claim 1 further comprising providing an alexandrite laser source to provide the beam of radiation having a wavelength at about 755 nm.

15. A method of treating a pigmentary abnormality disposed in an epidermal region and a vascular abnormality disposed in a dermal region of a target region of skin, comprising:
    providing a beam of radiation having a wavelength between about 700 nm and about 800 nm, a fluence of between about 80 J/cm$^2$ and about 100 J/cm$^2$, and a pulse duration between about 20 msec and about 60 msec;
    delivering, during a single pass of a delivery device, the beam of radiation to the target region of skin to affect (i) at least one pigmentary abnormality disposed in the epidermal region of the target region and (ii) at least one vascular abnormality disposed in the dermal region of the target region; and
    cooling a surface of the epidermal region of the target region of skin.

16. The method of claim 15 further comprising providing a dynamic cooling device to cool the epidermal region of the target region of skin.

17. The method of claim 15 wherein at least one pigmentary abnormality and at least one vascular abnormality are treated substantially simultaneously.

18. The method of claim 15 further comprising positioning, over the target region of skin, a delivery device capable of directing the beam of radiation to the target region of skin.

19. The method of claim 18 further comprising traversing the beam of radiation along the surface of the target region of skin to treat the at least one vascular abnormality and the at least one pigmentary abnormality during a single pass of the delivery device.

20. The method of claim 15 wherein the vascular abnormality comprises facial telangiectasia.

21. The method of claim 15 further comprising providing an alexandrite laser source to provide the beam of radiation having a wavelength at about 755 nm.

22. A method of treating a pigmentary abnormality disposed in an epidermal region and a vascular abnormality disposed in a dermal region on a patient's face, comprising:
    providing a beam of radiation having a wavelength between about 700 nm and about 800 nm, a fluence of between about 80 J/cm$^2$ and about 100 J/cm$^2$, and a pulse duration between about 20 msec and about 60 msec;
    delivering, during a single pass of a delivery device, the beam of radiation to a target region of skin of the patient's face to affect (i) at least one pigmentary abnormality disposed in the epidermal region of the target region and (ii) at least one vascular abnormality disposed in the dermal region of the target region; and
    cooling a surface of the epidermal region of the target region of skin.

23. The method of claim 22 further comprising providing a dynamic cooling device to cool the epidermal region of the target region of skin.

24. The method of claim 22 wherein at least one pigmentary abnormality and at least one vascular abnormality are treated substantially simultaneously.

25. The method of claim 22 further comprising positioning, over the target region of skin, a delivery device capable of directing the beam of radiation to the target region of skin.

26. The method of claim 25 further comprising traversing the beam of radiation along the surface of the target region of skin to treat the at least one vascular abnormality and the at least one pigmentary abnormality during a single pass of the delivery device.

27. The method of claim 25 further comprising providing an alexandrite laser source to provide the beam of radiation having a wavelength at about 755 nm.

* * * * *

UNITED STATES PATENT AND TRADEMARK OFFICE
CERTIFICATE OF CORRECTION

| | | |
|---|---|---|
| PATENT NO. | : 7,891,362 B2 | Page 1 of 1 |
| APPLICATION NO. | : 11/645222 | |
| DATED | : February 22, 2011 | |
| INVENTOR(S) | : Domankevitz et al. | |

It is certified that error appears in the above-identified patent and that said Letters Patent is hereby corrected as shown below:

In claim 4, at column 9, line 37, "a delivery device" should read as --the delivery device--.

In claim 5, at column 9, line 42, "a single pass" should read as --the single pass--.

In claim 18, at column 10, line 23, "a delivery device" should read as --the delivery device--.

In claim 19, at column 10, line 28, "a single pass" should read as --the single pass--.

In claim 25, at column 10, line 55, "a delivery device" should read as --the delivery device--.

In claim 26, at column 10, line 61, "a single pass" should read as --the single pass--.

Signed and Sealed this
Thirty-first Day of May, 2011

David J. Kappos
*Director of the United States Patent and Trademark Office*